United States Patent
Thurston (10) Patent No.: US 8,475,763 B2
(45) Date of Patent: Jul. 2, 2013

(54) METHOD OF DETERMINING THE COURSE OF TREATMENT FOR A PATIENT HAVING ADENOCARCINOMA

(75) Inventor: Marlin O. Thurston, Columbus, OH (US)

(73) Assignee: Actis, Ltd., Columbus, OH (US)

( * ) Notice: Subject to any disclaimer, the term of this patent is extended or adjusted under 35 U.S.C. 154(b) by 881 days.

(21) Appl. No.: 12/248,074

(22) Filed: Oct. 9, 2008

(65) Prior Publication Data

US 2010/0092392 A1    Apr. 15, 2010

(51) Int. Cl.
*A61K 51/10* (2006.01)
*A61K 49/04* (2006.01)

(52) U.S. Cl.
USPC .......................................... 424/1.49; 424/9.4

(58) Field of Classification Search
USPC ....................................................... 424/1.49
See application file for complete search history.

(56) References Cited

PUBLICATIONS

Sun et al., J. Surg. Oncolgoy 96: 297-308, 2007.*
Lee et al., J. of Nucl. Med 42: 764-769, 2001.*
Bakir et al., J. Nucl. Med. 33: 2154-2160, 1992.*
Grizzle et al, Arch. Parthol. Lab Med., 125: 91-98, 2001.*

* cited by examiner

*Primary Examiner* — Gyan Chandra
(74) *Attorney, Agent, or Firm* — Jerry K. Mueller, Jr.; Mueller Law, LLC (57) ABSTRACT

A method for detecting antigen associated with adenocarcinoma commences by forming a $^{124}$I conjugate of a preferential locator, such as an antibody, and introducing the conjugate into a patient suspected of having adenocarcinoma. Positron emission tomography (PET) scanning of the patient reveals sites of accumulated conjugate, such sites including lymph nodes. The course of treatment of the patient then is determined by the amount of revealed lymph nodes.

4 Claims, 3 Drawing Sheets

Primary Colon Cancer

Primary Renal Cell Cancer $^{18}$F FDG vs $^{124}$I-Mab

FDG

Humanized Monoclonal Antibody

RATIOS:

Tumor specific

Primary renal tumor

| 1. | Tumor/normal kidney | 9.5 to 1 |
| 2. | Tumor/liver | 11.4 to 1 |
| 3. | Tumor/aorta | 18.5 to 1 |

FIG. 3

RATIOS:

Tumor non-specific

Primary sigmoid tumor

| * | Tumor/colon | 1.7 to 1 |
| * | Tumor/liver | 1.2 to 1 |
| * | Tumor/bladder | None |

FIG. 4

RATIOS:

Primary renal tumor

| 1. | Tumor/normal kidney | 9.5 to 1 |
| 2. | Tumor/liver | 11.6 to 1 |
| 3. | Tumor/aorta | 18.5 to 1 |

FIG. 5

RATIOS:

Recurrent CRC
Liver metsX2

| 1 | Tumor/liver | 2.4 to 1 |
| 2 | Tumor/aorta | 2.7 to 1 |

FIG. 6

METHOD OF DETERMINING THE COURSE OF TREATMENT FOR A PATIENT HAVING ADENOCARCINOMA

CROSS-REFERENCE TO RELATED APPLICATIONS

None

STATEMENT REGARDING FEDERALLY SPONSORED RESEARCH

Not applicable.

BACKGROUND

The present disclosure generally relates to cancer and more particularly to pre-operatively locating and differentiating cancer involved lymph nodes for cancer patient prognostication or patient management.

In a story entitled "*Colon Cancer Care found Lacking*," by Lauran Neergard, Associated Press (Sep. 10, 2008), published in the *Boston Globe*, Neergard reports that nearly two-thirds of hospitals fail to check colon cancer patients well enough for signs that their tumor is spreading, says a study that advises patients to ask about this mark of quality care before surgery. National guidelines say that when colon cancer is removed, doctors should check at least 12 lymph nodes for signs of spread. Checking fewer than 12 isn't considered enough to be sure the cancer is contained. It is estimated that just 38% (of hospitals) fully comply with this guideline. Dr. Kyle Bilimoria of Northwestern University and The American College of Surgeons, and others describe shortcomings associated with colon cancer patient treatment in a study of 1,300 hospitals: "Some 148,000 Americans are diagnosed annually. For many, the node check can be crucial. Whether cancer has entered these doorways to the rest of the body is an important factor in long-term survival—and thus helps doctors decide who gets chemotherapy after surgery and who can skip it . . . . Patients who could benefit from additional chemotherapy may not be getting complete treatment and have a higher chance of relapse," said Dr. Durado Brooks of the American Cancer Society, who was not involved with the study. "It is something that consumers need to begin asking . . . . Frankly, that is most likely to change medical practice." "To check enough nodes, surgeons must remove enough of the fat tissue by the colon where they hide, and pathologists must painstakingly dissect that tissue to find the tiny nodes. Surgeons frequently tell of getting a pathology report of four clean nodes and asking the pathologist to find more, "and lo and behold, one of those additional nodes turns out to be positive," Bilimoria said.

In an article entitle, "Checking More Lymph Nodes Linked to Cancer Patient Survival", *ScienceDaily* (Jul. 23, 2008) reports: Why do patients with gastric or pancreatic cancer live longer when they are treated at cancer centers or high-volume hospitals than patients treated at low-volume or community hospitals? The report continues that new research from Northwestern University's Feinberg School of Medicine found that cancer patients have more lymph nodes examined for the spread of their disease if they are treated at hospitals performing more cancer surgeries or those designated as comprehensive cancer centers. Lymph node mestatases (indicating the spread of cancer) have been shown to predict patients' prognosis after cancer tissue is removed from the stomach or pancreas. If too few nodes are examined for malignant cells, a patient's cancer may be incorrectly classified, which alters the prognosis, treatment decisions and eligibility for clinical trials.

Referring to the Jul. 23, 2008 *ScienceDaily* article, "The differences in nodal evaluation may contribute to improved long-term outcomes at cancer centers and high-volume hospitals for patients with gastric and pancreatic cancer," said Karl Bilimoria, MD, lead author of the paper and a surgical resident at the Feinberg School." Bilimoria goes on to say: "Every reasonable attempt should be made to assess the optimal number of lymph nodes to accurately diagnose stage disease in patients with gastric and pancreatic cancer," said Bilimoria, who also is a research fellow at the American College of Surgeons. "The status of patients' lymph nodes is a powerful predictor of their outcome." July 2008 issue of *Archives of Surgery*.

Molecularimaging.net September 2008—Vol 2 No. 5, *Molecular Imaging Insight* (Sponsored by an educational grant from Siemens) states that the primary molecular imaging modalities—PET and SPECT—rely on biomarkers, or tracers, to help detect and localized disease. Current biomarkers, primarily FDG-based, which are used in oncologic and Alzheimer's applications, and cardiac tracers like 99mTc-Sestamibi, Rubidium-82 and N13-Ammonia, demonstrate the potential of molecular imaging. Used in conjunction with PET, FDG indicates metabolic activity associated with malignancies and is used in diagnosis, staging and monitoring treatment of various cancers. Despite their proven utility, there are limits to the currently available tracers. FDG uptake can be increased in benign disorders such as inflammation or infection potentially resulting in false positive results for cancer.

In a related article from the same issue of *Molecular Imaging Insight*, comes this discussion about disease detection and staging. PET scanning can be used to detect established tumors, but TAG positive lymph nodes are not detectable with today's PET agents. Also, PET agents produce non-specific positive results in the brain, heart, kidney, and inflammatory tissues. FDG opened the door and remains the gold standard for current oncology PET applications. It is approved for diagnosis and staging for a variety of types of cancer. But FDG also is associated with some shortcomings that make it a less than ideal tracer. For example, FDG is not highly specific. It does not always discriminate malignant from benign tumors, and uptake can be high in areas of inflammation. Consequently, it can be difficult for physicians to detect initial and recurrent disease in some patients, particularly those with inflammatory disease or scar tissue. In some cases, radiation therapy can produce scar tissue, decreasing the utility of FDG PET for disease monitoring as the tissue can obscure lesions. Molecularimaging.net September 2008—Vol 2 No. 5, *Molecular Imaging Insight*

FDG, then, is a sugar that is not a cancer-specific targeting agent. Tissues and organs that normally metabolize glucose—brain, heart, muscle, kidney, bladder, bowel—are visualized. Also imaged are inflammatory stricken tissue, infectious agents, and post-trauma engaged tissues.

FDG is indeed very easy to use. It is commercially available for PET scan. PET scan with FDG is a molecular imaging tool of the unique biochemical changes in tumors. $^{18}$F has a very short half-life (half-life 110 min.), which makes it a better isotope for handling and disposal within the operation room than $^{125}$I (half-life 60 days) in RIGS. However, $^{18}$F is not feasible for labeling of anti-TAG-72 antibody as it is in RIGS due the short half-life of $^{18}$F and long half-life of anti-TAG-72 antibodies, unless a two step system with $^{18}$F and anti-TAG-72 antibodies is modified for PET/CT image-guided surgery.

There are several limitations for PET and PET/CT image-guided surgery. First, this technology tends to detect the later stage tumors with resultant higher glycolysis rates. Therefore, this technology is somewhat limited by a finite level of tumor volume detection, such that small volume, microscopic, occult disease will be beneath the level of detection capable by PET and PET/CT image-guided surgery. Second, FDG is also taken up by many normal tissues and in many normal physiological conditions, such as is seen with brain, heart, kidney, muscle and adipose tissues. Duxin Sun, Mark Bloomston, George Hinkle, Osama Habib Al-Saif, Nathan C. Hall, Stephen P. Povoski, Mark W. Arnold, and Edward W. Martin Jr., "Advantages And Limitations Of Pet/Ct Image-Guided Surgery In Comparison To Hand-Held Detection Probe In RIGS", *Journal of Surgical Oncology* 2007; 96:297-308.

Newer biomarkers, such as FLT ($^{18}$F-3'-fluoro-3'-deoxy-L-thymidine), measure cell proliferation or cancer growth. Studies rate FLT as a better marker for tumor proliferation than FDG, but its uptake in cancer cells is lower than that of FDG. This means that whereas FDG does not generally detect tumors smaller than 5 mm, or lymph nodes, FLT is even worse in the cancer detection category.

*Journal of Nuclear Medicine* 2004, vol. 45, No. 9, pp 1509-1518; authors Maha Torabi, Suzanne L. Aquino, Mukesh G. Harisinghani, state:

> The accurate identification and characterization of lymph nodes by imaging has important therapeutic and prognostic significance in patients with newly diagnosed cancers. The presence of nodal metastases limits the therapeutic options and also generally indicates worse prognosis in patients. Thus, it becomes crucial to have this information before commencing therapy. Current cross-sectional imaging modalities rely on insensitive size and morphologic criteria and, thus, lack the desired accuracy for characterizing lymph nodes. This is mainly because metastases can be present in non-enlarged lymph nodes and not all enlarged nodes are malignant. PET has overcome some of these limitations but is still constrained by current resolution limits for small nodal metastases. This has fueled the development of targeted techniques for nodal imaging and characterization as outlined in this article.

Edmond S. Kassis, MD; Section of Thoracic Surgery, University of Pittsburgh Medical Center has been reported as saying that conventional scanning is inaccurate in over 40% of patients, as reported by Dr. Krasnack at the University of Maryland and by his group at the University of Pittsburgh. Endoscopic ultrasound is accurate in assessing the depth of tumor invasion, but its utility in detecting lymph node metastases has been questioned. Minimally invasive surgical staging has been shown by his group to be accurate, but requires general anesthesia and extensive lymph node dissection to avoid sampling errors, and requires a 24 to 48-hour hospital stay. Also, histological examination may miss small foci of metastatic disease, since there have been reports where up to 20% of histologically negative lymph nodes are positive on re-examination, which suggests a significant sampling error by pathologists. His group reports finding PET scanning to be useful in detecting distant metastatic disease, but only 44% sensitive in the detection of lymph node metastases.

Duxin Sun, Mark Bloomston, George Hinkle, Osama Habib Al-Saif, Nathan C. Hall, Stephen P. Povoski, Mark W. Arnold, and Edward W. Martin Jr., *Journal of Surgical Oncology* 2007; 96:297-308, in an article entitled "Radioimmunoguided Surgery (RIGS), PET/CT Image-Guided Surgery, and Fluorescence Image-Guided Surgery: Past, Present, and Future", state:

> FDG is indeed very easy to use. It is commercially available for PET scan. PET scan with FDG is a molecular imaging tool of the unique biochemical changes in tumors. $^{18}$F has a very short half-life (half-life 110 min.), which makes it a better isotope for handling and disposal within the operation room than $^{125}$I (half-life 60 days) in RIGS. However, $^{18}$F is not feasible for labeling of anti-TAG-72 antibody as it is in RIGS due the short half-life of $^{18}$F and long half-life of anti-TAG-72 antibodies, unless a two step system with $^{18}$F and anti-TAG-72 antibodies is modified for PET/CT image-guided surgery.
>
> There are several limitations for PET and PET/CT image-guided surgery. First, this technology tends to detect the later stage tumors with resultant higher glycolysis rates. Therefore, this technology is somewhat limited by a finite level of tumor volume detection, such that small volume, microscopic, occult disease will be beneath the level of detection capable by PET and PET/CT image-guided surgery. Second, FDG is also taken up by many normal tissues and in many normal physiological conditions, such as is seen with brain, heart, kidney, muscle and adipose tissues.

These authors conclude:

> Humanized HuCC49ΔCH$_2$ is the optimal antibody for tumor detection and has no HAMA response. RIGS with anti-TAG-72 antibodies [HuCC49ΔCH$_2$] not only detects gross tumor, but also allows for precise detection and localization of occult disease within adjacent tissues and regional lymph nodes. The successful detection and subsequent removal of such occult disease in cancer patients significantly improve the 10-year survival.

Ismet Sarikaya, Stephen P Povoski, Osama H Al-Saif, Ergun Kocak, Mark Bloomston, Steven Marsh, Zongjian Cao, Douglas A Murrey, Jun Zhang, Nathan C Hall, Michael V Knopp, and Edward W Martin, Jr., *World J Surg Oncol.* 2007; 5: 80, Published online Jul. 16, 2007. doi: 10.1186/1477-7819-5-80, in an article entitled, "Combined use of preoperative $^{18}$F FDG-PET imaging and intraoperative gamma probe detection for accurate assessment of tumor recurrence in patients with colorectal cancer", state:

> Numerous studies have demonstrated that FDG-PET has high sensitivity and high specificity for the detection of tumor recurrence in CRC patients with rising CEA levels in which there are no identifiable sites of tumor recurrence by standard anatomical imaging methods. Particularly, combined PET/CT is superior to CT and MRI for the detection of CRC local recurrences, as well as metastatic disease to the liver and other distant sites. However, the current FDG-PET scanning systems have several limitations. One of the most important limitations of FDG-PET scanning is its low sensitivity in detecting small sized lesions. FDG-PET has limited ability to detect lesions measuring less than 5 to 10 mm in size. A second limitation of FDG-PET imaging is the limited ability to assess local tumor invasion into the surrounding tissues. Strictly speaking, PET only imaging cannot identify local tumor invasion into the surrounding tissues secondary to the absence of anatomical correlation, as can be provided by combined PET/CT imaging. Nevertheless, while combined PET/CT imaging may be helpful in this regard if deeper tumor invasion is present, it will not be able to assess more limited tumor invasion. An additional limitation of FDG-PET imaging is its limited sensitivity for the detection of tumors that display a low metabolic activity. Finally, $^{18}$F FDG is limited by the fact that it is not cancer-specific, and resultant physiological uptake into benign tissue processes, such as infection and inflammation, can result in the identification of areas of increased uptake of $^{18}$F FDG."

A recognizable limitation to both FDG-PET imaging and intraoperative GP [gamma probe] detection is the physiologic $^{18}$F FDG activity which can be demonstrated within nonmalignant tissues. This is especially evident in the scenario in which increased $^{18}$F FDG activity is seen in associated with infectious and/or inflammatory changes within nontumor-bearing tissues. Such a scenario creates false positive results with both preoperative FDG-PET imaging and intraoperative GP detection techniques. Likewise, it is well established that mucinous tumors are more difficult to identify with FDG-PET imaging, likely secondary to a lower metabolic activity of such tumors. It has been previously reported that the sensitivity of FDG-PET imaging for the detection of mucinous carcinoma is significantly lower than that of nonmucinous carcinoma (58% and 92%, respectively). This would also be the expectation for intraoperative GP detection of $^{18}$F FDG. Nevertheless, in our current study, the sites of tumor recurrence were accurately detected by both FDG-PET imaging and intraoperative GP detection in those three patients whose CRC recurrence represented mucinous adenocarcinoma. Although previous studies suggest that both preoperative FDG-PET imaging and intraoperative GP detection may not as effectively identify mucinous tumors, the surgeon's ability to position the intraoperative GP in close proximity to sites of suspected tumor recurrence may ultimately make intraoperative GP detection more efficient for the detection of mucinous tumors as compared to preoperative FDG-PET imaging.

MacManus, et al, Department of Radiation Oncology, Peter MacCallum Cancer Centre, East Melbourne, Victoria, Australia are reported as saying that PET scanning, because of its impressive sensitivity and accuracy, is being incorporated into the standard staging workup for many cancers. These include lung cancer, lymphomas, head and neck cancers, and oesophageal cancers. PET often provides incremental information about the patient's disease status, adding to the data obtained from structural imaging methods, such as, CT scan or MRI. PET commonly upstages patients into more advanced disease categories. Incorporation of PET information into the radiotherapy planning process has the potential to reduce the risks of geographic miss and can help minimize unnecessary irradiation of normal tissues. The best means of incorporating PET information into radiotherapy planning is uncertain, and considerable effort is being expended in this area of research.

The boundaries of some tumours can be very difficult to define, especially those that do not have clearly delineated margins on CT component of PET/CT. Motion of the patient on the couch top, which should be minimal with appropriate positioning and immobilization, and internal motion also contribute to the blurriness of PET images. Other factors that commonly cause difficulty include regions of low avidity in the tumour due to necrosis, the confounding effects of inflammation and infection that can give rise to intense uptake well within the range of standardized uptake value (SUV) seen in tumours, and poor contrast between tumours with a low SUV and adjacent normal structures. PET information is acquired over many respiratory and cardiac cycles and, therefore, an "average" position of the structures is imaged. In contrast, CT image is acquired virtually instantaneously and usually at a random phase of the respiratory cycle. *Biomed Imaging Interv* J 2007; 3(1):e4 doi: 10.2349/biij.3.1.e4

Maha Torabi, MD, Suzanne L. Aquino, MD; and Mukesh G. Harisinghani, MD, Department of Radiology, Massachusetts General Hospital, Boston, Mass. state that the accurate identification and characterization of lymph nodes by imaging has important therapeutic and prognostic significance in patients with newly diagnosed cancers. The presence of nodal metastases limits the therapeutic options and also generally indicates worse prognosis in patients. Thus, it becomes crucial to have this information before commencing therapy. Current cross-sectional imaging modalities rely on insensitive size and morphologic criteria and, thus, lack the desired accuracy for characterizing lymph nodes. This is mainly because metastases can be present in non-enlarged lymph nodes and not all enlarged nodes are malignant. PET has overcome some of these limitations but is still constrained by current resolution limits for small nodal metastases. This has fueled the development of targeted techniques for nodal imaging and characterization as outlined in this article. In the past few years, studies have shown that these newer imaging techniques can bridge some of the limitations of existing imaging for nodal characterization and thereby provide the much-needed staging information before the initiation of therapy. *Journal of Nuclear Medicin*. Vol. 45 No. 9 1509-1518.

U.S. Published Application 2007/0104717 discloses antibodies directed against CD55 and CD97 that can be used in PET scanning to detect and diagnose adenocarcinoma of the prostate (Paragraphs [0169], [0021]; Claim 18). Labels include Indium-111, Tc-99m, $^{131}$I, Gd (III) and Mn (II).

U.S. Published Application 2007/0042432 discloses a method of diagnosing adenocarcinoma using antibodies in PET scanners (Paragraphs [0140]-[0146]; Claim 14). No specific labels are shown.

U.S. Published Application 2006/0275212 discloses a method of diagnosing adenocarcinoma of the prostate using antibodies against prostate membrane antigen protein in a PET scanner (Paragraphs [0075]-[0076]; Claim 21). Labels include $^{131}$I, $^{111}$In $^{123}$I, $^{99m}$Tc, $^{32}$P, $^{125}$I, $^{3}$H, $^{14}$C, and $^{188}$Rh.

U.S. Published Application 2006/0088539 discloses a method of using modified antibodies to prostate membrane antigen protein to detect adenocarcinoma of the prostate by PET scanning (Paragraphs [0435]-[0436]). Labels include $^{131}$I, $^{111}$In $^{123}$, $^{99m}$Tc, $^{32}$P, $^{125}$I, $^{3}$H, $^{14}$C, and $^{188}$Rh.

Despite the perceived "advances" in cancer patient management by dint of PET scanning, John L. Marshall, MD (Chief, Division of Hematology/Oncology, Director of Development Therapeutics and GI Oncology, Lombardi Comprehensive Cancer Center, Georgetown University) takes a contrary position in "Practice-Changing Implications Today Compelling Data for Tomorrow" in a review of oncology PET scanning for the 44$^{th}$ Annual Meeting of the American Society of Clinical Oncology for their annual May/June 2008 meeting. In his review, Dr. Marshall notes that. "the role of PET scanning in the management of colorectal liver metastasis is controversial". He continues that, "there is a relatively high false-positive and false-negative rate in patients with metastatic disease". In fact, the "tumor size must be at least 1 cm to be reliably detected." In a study reviewed, he notes, that "there still is a 28% rate of futile surgery performed." He concludes that, "it is clear that we need even better imaging techniques to assist our decision making when attempting aggressive, invasive, although curative in intent, operations." Supplement, Desk Reference, September 2008 *Oncology*, p. 17.

Thus, there still is a need to preferentially detect cancer-related lymph nodes, as well as tumors) preoperatively and in a facile manner, especially in order to enable the attending physician to determine the proper course of treatment (prognostication) of each such patient. It is to such need that the present disclosure is addressed.

BRIEF SUMMARY

A method for detecting lymph node-involved antigen associated with cancerous tissue, such as, for example, an adenocarcinoma, commences by forming a $^{124}$I conjugate of a preferential locator, such as a monoclonal antibody, and introducing the conjugate into a patient suspected of having cancerous tissue. Preoperative positron emission tomography (PET) scanning of the patient reveals sites of accumulated conjugate, such sites including lymph nodes. The course of treatment of the patient—including, inter alia, pre-operative chemotherapy, post-operative chemotherapy, scope of surgery (if any), duration of chemotherapy, number of courses of chemotherapy, and the like—then is determined by the amount of revealed lymph nodes.

BRIEF DESCRIPTION OF THE DRAWINGS

For a fuller understanding of the nature and advantages of the present process, reference should be had to the following detailed description taken in connection with the accompanying drawings, in which.

DETAILED DESCRIPTION

Traditional imaging of cancer patients has revealed little useful patient management data. The same is true for PET imaging, due in part to ineffective detectable locators that are overwhelmed by background. This is proven, since effective PET imaging of surgically removed samples (ex vivo samples) occurs. What is needed, then, is a preferential locator that binds to antigen in lymph node tissue and which patient PET imaging, both preoperatively and postoperatively, reveals both tumors and lymph node tissue with background being minimized.

Preferential Locators

Tumor-associated antigen (TAG-72) is a human mucin (MUC1) like glycoprotein complex with molecular weight of $10^6$ Da. It is over-expressed in several epithelial-derived cancers, including most ductal carcinomas of the breast, common epithelial ovarian carcinomas, non-small cell lung carcinomas, gastric, pancreatic, and colorectal carcinomas. Murine monoclonal antibody (B72.3) was generated using membrane-enriched extracts of human metastatic mammary carcinoma lesions, while the second generation monoclonal antibody (CC49) was generated against purified TAG-72 from colon cancer. These antibodies have been extensively evaluated in animal models and human for detection of various cancers, one of which has been approved by FDA for the detection of both colorectal and ovarian cancers with in gamma camera scanning in conjunction with computerized tomography. ($^{111}$Indium labeled B72.3 antibody, CYT-103, Cytogen).

TAG-72 antibody shows selective reactivity for human carcinomas, demonstrating that 94% of colon carcinomas express the TAG-72, while normal colon epithelium does not show any reactivity to the antibody. Murine monoclonal B72.3 also reacted with cells in areas of "atypia" within adenomas. It also showed reactivity with other human carcinomas including 84% of invasive ductal breast cancer, 100% of ovarian cancers tested, and 96% lung of adenocarcinomas, while it showed only weak or no reactivity in the corresponding normal tissues except secretory endometrium.

B72.3 antibody has been evaluated in tissue culture and xenograft models. Interestingly, this antibody is not reactive to vast majority of human carcinoma cell lines in cultures due to limitations in this special configuration. However, it is highly expressed in colon cancer cell lines (e.g., LS 174T) and breast cancer cells lines (e.g., MCF-7). When these cells were grown in spheroid culture, suspension cultures or on agar, TAG-72 expression increased by 2-10 fold. Additionally, when the LS 174T cell line was injected into athymic mice to generate xenograft models, the level of TAG-72 antigen increased over 100-fold, which is similar to expression levels seen in the metastatic tumor masses from patients. $I^{125}$-labeled B72.3 was tested in xenograft mice models with LS-174 cancer cells for tumor localization. After intravenous injection of 1.5 μCi of $^{125}$I-labeled B72.3, 10% of injected dose per gram of body weight (% ID/g) was determined after two days. Interestingly, the total amount of $^{125}$I-B72.3 activity in the tumor stayed constant during 30 days, while the activity in the rest of the body including blood, kidney, liver, spleen, and lung decreased significantly. For example, The % ID/g of $^{125}$I-B72.3 in tumors stayed at 6.49% to 10.75% in 7 days period, while it decreased from 9.94% to 1.38% in blood, 1.82% to 0.34% in kidney, 2.23% to 0.37% in spleen, 5.52% to 0.75% in lung, and 1.89% to 0.37%. The distribution ratio of tumor compared to other normal organs (liver, kidney, lung) reached 18:1 at day 7, while tumor to blood ratio reached 5:1 at day 7. In xenograft models with A375 cells without TAG-72 expression, B72.3 did not show any tumor localization. In xenograft models implanting LS 174T with high levels of TAG-72, other control antibodies such as $^{125}$I-MOPC-21 IgG did not show tumor localization either.

$^{131}$I labeled B72.3 IgG has been used clinically for diagnostic imaging of colorectal, ovary, and breast cancer. The data demonstrate the specific localization of B72.3 antibody in cancer tissues in patients. After intravenous (IV) administered $^{131}$I-labeled B72.3 IgG prior to surgery, radio-localization indices (RI) were calculated by cpm of $^{131}$I-labeled antibody per gram of tumor versus cpm per gram of normal tissues. Seventy percent (99 of 142) of tumor lesions showed RI is of greater than 3 (antibody localization in tumors is 3 times greater than normal tissue). In addition, high-performance liquid chromatography (HPLC) and SDS-polyacrylamide gel electrophoresis demonstrated that the radioactivity in patient's sera was associated with intact $^{131}$I-B72.3 antibody as visualized in autoradiography or IgG peak in HPLC analysis after IV administration of dose range 0.5-20 mg. Interestingly, when $^{131}$I-labeled B72.3 IgG was administered intraperitoneally in colon cancer patients, the localization in colon tumor verse normal tissue was 70:1. However, IV administration of this labeled antibody is more efficient in targeting lymph node metastases.

$^{125}$I-labeled B72.3 also has been used for radio-immunoguided surgery (RIGS®, U.S. Pat. No. 4,782,840) with an intraoperative hand-held probe to localize the residual tumor tissue for resection. The RIGS system also has been successfully used with the B72.3 antibody for clinical colorectal cancer patients. $^{125}$I labeled-antibody has localized 75%-80% of primary colorectal tumor lesion, and 63%-73% of metastatic lesions in lymph nodes and liver.

The second-generation antibody CC49 was generated against TAG-72 purified from colon cancer. CC49 showed higher binding affinity than B72.3 to TAG-72 in carcinomas including breast, colorectal, ovarian, and lung carcinomas, while CC49 exhibited minimum reactivity with normal tissues. When $^{125}$I-CC49 was administered in xenograft models with colon cancer cells LS 174T, the plasma clearance was much faster than B72.3, which results in much higher tumor to normal tissue distribution ratio. For example, the tumor to blood ratio was 18.1, tumor to liver ratio 3.81, tumor to spleen ratio 16.64, tumor to kidney ratio 36.48, and tumor to lung ratio 25.82. In RIGS studies of 300 patients with colorectal cancers, CC49 was able to successfully detect tumors in 86% of patients with primary tumors and 95% of patients with recurrent tumors. In addition, clinical studies of a modified humanized antibody CC49$\Delta C_H 2$ with a deletion in glycosylation sites of the antibody showed similar results with CC49 in detection of colorectal cancer. See, for example, the following reported clinical trial: Pilot Study Using a Humanized CC49 Monoclonal Antibody (HuCC49deltaCH2) to Localize Recurrent Colorectal Carcinoma Doreen M. Agnese, MD, Shahab F. Abdessalam, MD, William E. Burak, Jr., MD, Mark W. Arnold, MD, Denise Soble, RN, George H. Hinkle, RPh, Donn Young, PhD, M. B. Khazalaeli, PhD, and Edward W. Martin, Jr., MD *Annals of Surgical Oncology*, 11(2): 197-202; and Pharmacokinetics and Clinical Evaluation of $^{125}$I-Radiolabeled Humanized CC49 Monoclonal Antibody (HuCC49deltaCH2) in Recurrent and Metastatic Colorectal Cancer Patients Jim Xiao, Sara Horst, George Hinkle, Xianhua Cao, Ergun Kocak, Jing Fang, Donn Young, M. Khazaeli, Doreen Agnese, Duxin Sun, and Edward Marting, Jr., *Cancer Biotherapy & Radiopharmaceuticals*, Volume 20, Number 1, 2005. See also, Agnese, et al., "Pilot Study Using CC49 Monoclonal Antibody (HuCC49$\Delta CH_2$) to Localize Recurrent Colorectal Carcinoma", *Annals of Surgical Oncology* 11(2): 197-202 ("TAG-72 is an antigen expressed in several epithelial-derived cancers, including most colonic adenocarcinomas, invasive ductal carcinomas of the breast, non-small cell lung carcinomas, common epithelial ovarian carcinomas, and most pancreatic, gastric and esophageal cancers evaluated."); Thor, et al., "Distribution of Oncofetal Antigen Tumor-associated Glycoprotein-72 Defined by Monoclonal Antibody B72.3" *Cancer Research* 46, 3118-3124, June 1986, (TAG-72 was shown to be expressed in several epithelial-derived cancers including 94% of colonic adnocarcinomas, 84% of invasive ductal carcinomas of the breast, 96% of non-small cell lung carcinomas, 100% of common epithelial ovarian carcinomas, as well as the majority of pancreatic, gastric and esophageal cancers evaluated. TAG-72 expression was not observed, however, in tumors of neural, hematopoietic, or sarcomatous derivation, suggesting that the TAG-72 antigen is "pancarcinoma" in nature. Appreciable monoclonal antibody B72.3 reactivity was generally not observed in adult normal tissues, with limited reactivity noted in a few benign lesions of the breast and colon. TAG-72 antigen expression was detected, however, in fetal colon, stomach, and esophagus, thus defining TAG-72 as an oncofetal antigen.").

Both B72.3 and CC49 have demonstrated promising results in tumor detection utilizing the RIGS procedure to significantly improve patient survival rate. However, in many cases, patients have shown metastatic cancers or multiple lesions, which are not resectable. In such cases, even though the antibodies used with RIGS are able to detect the tumors, surgery cannot be employed to remove the tumors. The long half-life of $^{125}$I, waste disposal of $^{125}$I, and other problems associated with $^{125}$I also make this procedure difficult for the market to accept. Other labels, such as, for example, $^{18}$F with a 110-minute half life, will not work in this procedure, because of the need to wait 21 days after antibody injection in order for non-bound antibody to clear the body.

Thus, antibody CC49, its humanized and domain deleted forms, and related TAG antibodies have been described in the literature, such as, by Xiao, et al., "Pharmocokinetics and clinical evaluation of $^{125}$I-radiolabeled humanized CC49 monoclonal antibody (HuCC49$\Delta C_H 2$) in recurrent and metastatic colorectal cancer patients", *Cancer Biother Radiopharm*, vol. 20, number 1, 2005; Fang, et al., "Population pharmocokinetics and tumor targeting of HuCC49$\Delta$CH2, a novel monoclonal antibody for tumor detection", Fang, et al., *J Clin Pharmacol* 2007; 47:227-237; U.S. Pat. Nos. 6,418, 338 and 6,760,612 (which also show peptide, lectin, and other detector molecules. See also, Slavin-Chiorini, et al., "A CDR-Grafted (Humanized) Domain-Deleted Antitumor Antibody", *Cancer Biotherapy and Radiopharmaceuticals*, Volume 12, Number 5, 1997, Mary Ann Liebert, Inc. ("The MAb chosen for engineering was CC49, which is directed against a pancarcinoma antigen designated TAG-72 that is expressed on the majority of colorectal, gastric, breast, ovarian, prostate, pancreatic and lung carcinomas.").

Yet another humanized antibody of CC49 MAb is known as V59. Gonzales, et al., "Minimizing immunogenicity of the SDR-grafted humanized antibodyCC49 by genetic manipulation of the framework residues", *Molecular Immunology* 40 (2003) 337-349. V59 is reported to be a fully humanized version of CC49 MAb, making it a likely choice for use in accordance with the disclosure set forth herein.

In the early 1990s investigators utilized the RIGS system to locate, differentiate and stage other types of cancer, for instance, endocrine tumors involved, inter alia, with breast, children, gastrinomas, lung and nervous system. Generally, the approach was to administer a radiolabeled somatostatin congener to assess the patient with the RIGS probe. However, before subjecting the patient to such administration, an initial determination preferably was made as to whether the radiolabeled somatostatin congener would bind to the tumor site, i.e., whether somatostatin receptors are associated with the neoplastic tissue. This was conveniently done with a wide variety of endocrine tumors, which release peptides or hormones, referred to as "biochemical markers." In order to make this determination, initially a biochemical marker-inhibiting dose of unlabeled somatastatin congener was administered to the patient. The biochemical marker associated with the neoplastic tissue then was monitored to determine whether the administered somatostatin congener reduces the presence of the marker in the patient. If the monitored presence of the marker was reduced, then the surgeon could be confident that the neoplastic tissue or tumor contains receptors to which the somatostatin would bind. Thus, the administration of radiolabeled somatostatin congener was appropriate for such patient. If the biochemical marker associated with the neoplastic tissue was not appropriately reduced following the administration of the unlabeled somatostatin congener, then the neoplastic tissue may not be determinable by the use of radiolabeled somatostatin congener and alternative modalities of treatment would be considered, such as the use of radiolabeled antibodies. See: O'Dorisio, et al., U.S. Pat. No. 5,590,656; entitled "Application of Peptide/Cell Receptor Kinetics Utilizing Radiolabeled Somatostatin Congeners in the In Situ, In Vivo Detection and Differentiation of Neoplastic Tissue"; issued Jan. 7, 1997 and incorporated herein by reference.

In broader contexts, a locator that specifically binds a marker produced by or associated with neoplastic tissue is used in accordance with the present teachings, with antibodies and somatostatin congener being representative such locators. Broader, however, a "locator" includes a substance that preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778, incorporated herein by reference) and like substances have been developed and may similarly prove efficacious. For example, genetic engineering has been used to generate a variety of modified antibody molecules with distinctive properties. These include various antibody fragments and various antibody formats. An antibody fragment is intended to mean any portion of a complete antibody molecule. This includes both terminal deletions and protease digestion-derived molecules, as well as immunoglobulin molecules with internal deletions, such as deletions in the IgG constant region that alter Fc mediated antibody effector functions. Thus, an IgG heavy chain with a deletion of the Fc CH2 domain is an example of an antibody fragment. It is also useful to engineer antibody molecules to provide various antibody formats. In addition to single chain antibodies, useful antibody formats include divalent antibodies, tetrabodies, triabodies, diabodies, minibodies, camelid derived antibodies, shark derived antibodies, and other antibody formats. Aptomers form yet a further class of preferential locators. All of these antibody-derived molecules are example of preferential locators.

In addition to antibodies, biochemistry and genetic engineering have been used to produce protein molecules that mimic the function of antibodies. Avimers are an example of such molecules. See, generally, Jeong, et al., "Avimers hold their own", *Nature Biotechnology* Vol. 23 No. 12 (December 2005). Avimers are useful because they have low immunogenicity in vivo and can be engineered to preferentially locate to a wide range of target molecules such as cell specific cell surface molecules. Although such substances may not be subsumed within the traditional definition of "antibody", avimer molecules that selectively concentrate at the sites of neoplastic tissue are intended to be included within the definition of preferential locator. Thus, the terms "locator" was chosen, to include present-day antibodies and equivalents thereof, such as avimers, as well as other engineered proteins and substances, either already demonstrated or yet to be discovered, which mimic the specific binding properties of antibodies in the inventive method disclosed therein.

Thus, while monoclonal antibodies can be used to advantage in the present disclosure and will be used herein to illustrate the precepts disclosed herein, as noted above, a variety of additional detector molecules for markers associated with cancer cells (TAG), are suitable for use in the present context. Thus, detector molecule should be interpreted broadly for present purposes.

Iodine-124 ($^{124}$I)

$^{124}$I is a positron-emitting isotope of iodine with a half-life of approximately 4 days. Satisfactory positron-emission tomography (PET) imaging is feasible for up to a week following administration of $^{124}$I. For the same administered activities of the same radioiodinated radiopharmaceutical, the normal-tissue radiation doses with iodine-124 are comparable to or less than those with iodine-131. Studies have shown that imaging and quantification of $^{124}$I using a dedicated PET system is comparable to that with $^{18}$F, which is a widely used tracer [Juweid, M. E. & Cheson, B. D., "Positron-emission tomography and assessment of cancer therapy", *N. Engl. J. Med.* 354, 496-507 (2006)]. Therefore, comparable amounts of isotope may be administered to give virtually identical resolution and sensitivity characteristics. Bendriem, B., Finn, R. D., Jordan, K., Kalaigian, H., Karp, J. S., Robeson, W. R., & Larson, S. M, "Quantitative imaging of iodine-124 with PET. *J. Nucl. Med."*, 37, 1557-1562 (1996); Pentlow, K. S., Graham, M. C., Lambrecht, R. M., Cheung, N. K., & Larson, S. M., "Quantitative imaging of I-124 using positron emission tomography with applications to radioimmunodiagnosis and radioimmunotherapy", *Med. Phys.* 18, 357-366 (1991); Divgi, et al. *Lancet Oncol* 2007; 8:304-10.

Antibodies can be bound to $^{124}$I by the same procedures used to bind $^{125}$I and $^{131}$I to an antibody, such as described in, for example, U.S. Pat. Nos. 4,782,840 and 5,185,142, and references cited therein.

Prognosis of Positron Emission Tomography (PET) Scanned Patients

The ability of intraoperative probing of cancer patients administered $^{125}$I labeled CC49 MoAb to stage cancer patients was disclosed in U.S. Pat. No. 5,482,040 issued Jan. 9, 1996, and incorporated herein by reference. The key to such disclosed biostaging was the recognition of lymph node involvement and the relationship between probe position tissue and patient long-term survival. These data are reported by Arnold, et al., in "Intra-Abdominal Patterns of Disease Dissemination in Colorectal Cancer Identified Using Radioimmunoguided Surgery", *Dis Colon Rectum, Vol.* 39, No. 5, May 1996, 509-513, and incorporated herein by reference. Of course, surgery of a patient is required in order to biostage the patient. There would be patient benefit to biostaging a cancer patient by external imaging prior to surgery. Such protocol would obviate surgery of non-resectable patients and enable early therapeutic intervention (e.g., chemotherapy, radiation, etc.). Unfortunately, external imaging of cancer-involved lymph nodes has yet to be achieved. Barbera-Guillem, et al., "First Results for Resetting the Antitumor Immune Response by Immune Corrective Surgery in Colon Cancer" *The American Journal of Surgery* Volume 176 October 1998 (339-343) confirms the importance of lymph node removal.

A good review comparing RIGS surgery, PET/CT immuno-guided surgery, and fluorescence guided surgery is given by Sun, et al., "Radioimmunoguided Surgery (RIGS), PET/CT Image-Guided Surgery, and Fluorescence Image-Guided Surgery: Past, Present, and Future", *J Surg Oncol* 2007; 96:297-308, incorporated herein by reference. The shortcomings of these techniques is explained by Sun, et al., as well as the long term survival of patients that were RIGS negative following resection. Sun, et al. concludes that three generations of anti-TAG-72 antibodies have been evaluated in clinical trials. He describes the most recently developed humanized HuCC49ΔCH2, which exhibited no HAMA in human use, as the optimal candidate for tumor detection. The use of these anti-TAG-72 antibodies enables precise detection and localization of occult tumor in adjacent tissue and regional lymph nodes. Sun then addresses the importance of the removal of occult disease to 10-year survival. The article concludes that PET tends to detect later stage disease and resultantly has more limited success for earlier stage disease when tumor volume is smaller (as well as lymph nodes which he should have addressed here). The article motivates the artisan to involve a radiolabel without the long half-life of $^{125}$I and associated handling problems, along with a detection technique that responds to early stage disease, as well as late-stage disease.

The following table demonstrates the inability to determine involved lymph nodes by traditional means.

| RECURRENT COLORECTAL CANCERS* | | | |
|---|---|---|---|
| Sites Identified | Traditional N = 45 (%) | CC49 I$^{125}$ N = 45 (%) | FDG F$^{18}$ N = 25 (%) |
| Liver | 29 (64) | 29 (64) | 8 (32) |
| Diaphragm | 11 (24) | 13 (29) | 2 (8) |
| Gastrohepatic ligament | 8 (18) | 30 (67) | 2 (8) |
| Celiac | 5 (11) | 22 (49) | 0 (0) |
| Retroperitoneal | 4 (9) | 5 (11) | 6 (12) |
| Small bowel mesentery | 11 (24) | 13 (29) | 1 (4) |
| Abdominal wall | 11 (24) | 10 (22) | 1 (4) |
| Omental | 3 (7) | 6 (13) | 2 (8) |
| Anastamotic | 3 (7) | 3 (7) | 3 (12) |
| Pelvis | 19 (42) | 22 (49) | 12 (49) |
| Iliac | 8 (18) | 14 (31) | 2 (8) |
| Sacral prominence | 1 (2) | 2 (4) | 0 (0) |
| Total | 116 (100) | 184 (100) | 41 (100) |
| Year | 1996 | 1996 | 2007 |

Figure 1:
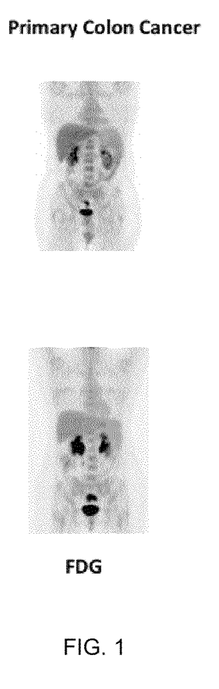
FIG. 1 shows a primary colon cancer patient imaged with $^{18}$F FDG. Organs show up, as well as the tumor.
Figure 2:
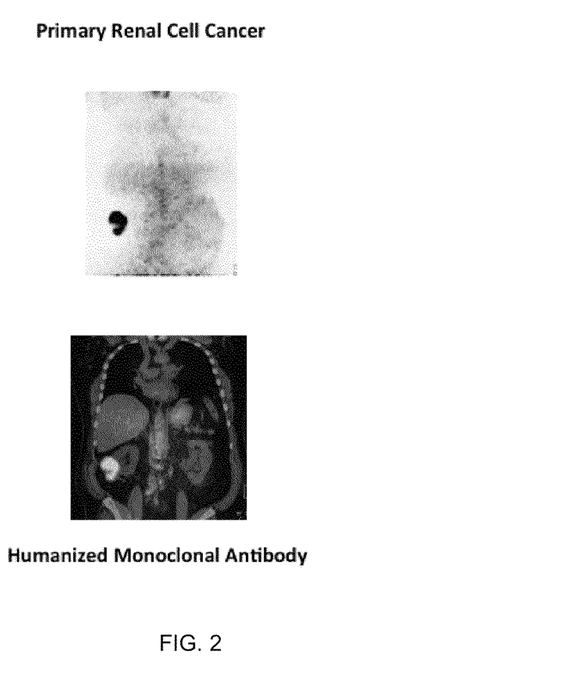
FIG. 2 shows primary renal cell cancer imaged with $^{124}$I cG250. The primary tumor images nicely.
Figure 3:
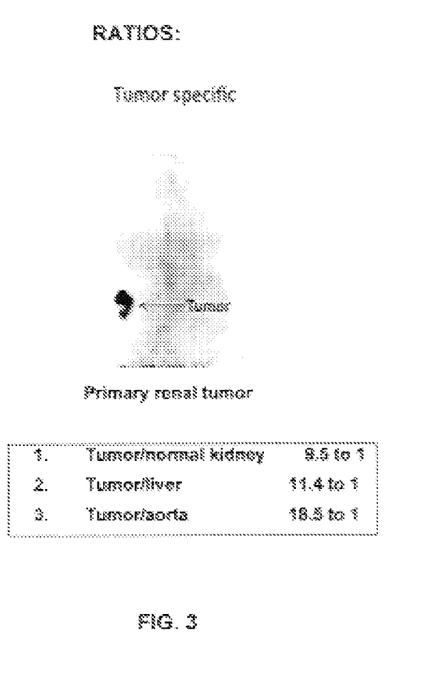
FIGS. 3 and 4 show primary renal cell cancer using $^{124}$I cG250. Tumor ratios are provided along with tumor location.
Figure 4:
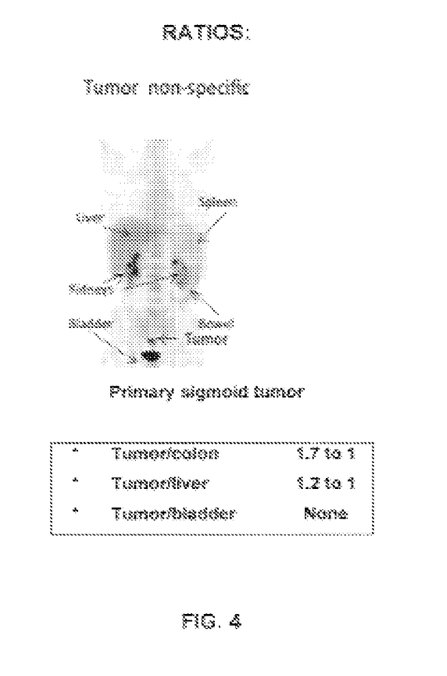
Figure 5:
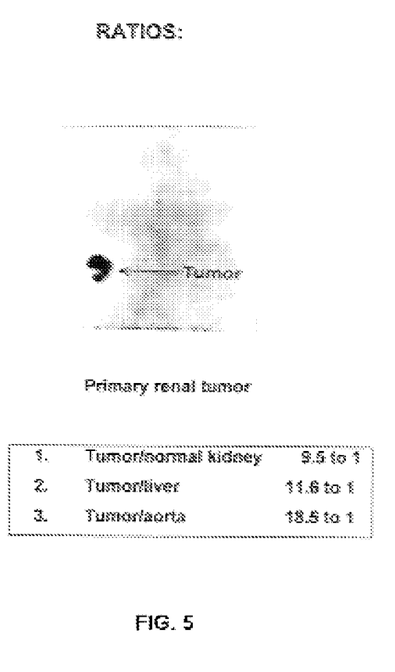
FIGS. 5 and 6 show recurrent renal cell cancer using $^{124}$I cG250. Tumor ratios are provided along with tumor location.
Figure 6:
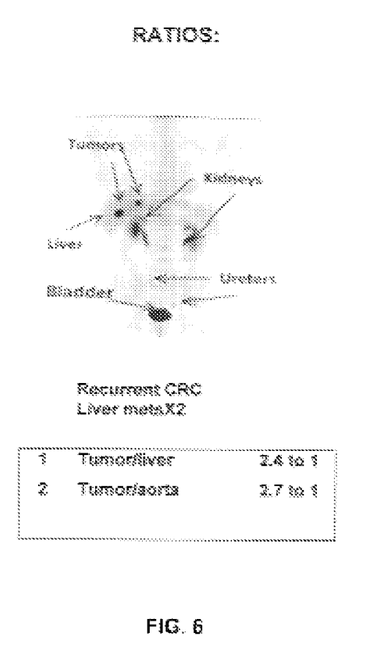

*Data from Arnold, et al., Dis Colon Rectum, Vol. 39, No. 5, May 1996, 509-513, supra; and Sun, et al., J Surg Oncol 2007; 96: 297-308, supra This also is demonstrated in the drawings. Particularly, FIG. 1 shows a primary colon cancer patient imaged with $^{18}$F FDG. Organs show up, as well as the tumor. FIG. 2 shows primary renal cell cancer imaged with $^{124}$I cG250. The primary tumor images nicely. Tumor ratios are provided along with tumor location for primary renal cell cancer (FIGS. 3 and 4) and for recurrent renal cell cancer (FIGS. 5 and 6), again using $^{124}$I cG250. However, neither FDG or cG250 images lymph nodes.

The method disclosed herein recognizes the ability of PET scanning to image $^{124}$I administered to patients and the ability of certain known preferential locators to accrete at the sites of antigen associated with neoplastic tissue, such as renal carcinoma using $^{124}$I labeled chimeric G250, as reported by Divgi, et al., supra. Thus, the initial step involves the formation of a conjugate of $^{124}$I and a preferential locator, such as, a monoclonal antibody, for example, antibody CC49, its humanized and domain deleted forms. The conjugate then is introduced into a patient suspected of having adenocarcinoma. The patient then is subjected to positron emission tomography (PET) scanning to reveal sites of accumulated conjugate, said sites including lymph nodes. The course of treatment of said patient then is determined by the amount of revealed lymph nodes, i.e., the patient is biostaged.

Such method enables the oncologist to avoid surgery on non-resectable patients and to administer therapy suitable for the cancer stage of the patient, often resulting in sufficient cytoreduction that surgery then can be undertaken. This method is enabled by the recognition that patient prognosis can be aided by PET scanning of patients administered preferential locators labeled with $^{124}$I.

EXAMPLES $^{124}$I-HuCC49ΔCH2-PET Tumor Imaging in Animal Model

Material and Methods

Since $^{124}$I is a positron emitter with only 4.2 days half life, it not only relatively easy to handle and dispose the surgical tissues, but also can produce a high resolution positron emission tomography (PET) image using a readily available PET scanner. Therefore, $^{124}$I-HuCC49ΔCH2 labeling may be suitable for both tumor imaging and detection.

Iodination ($^{124}$I) of HuCC49ΔCH2

Iodogen-Coated Vials:

Iodogen (1,3,4,6-tetrachloro-3α-6α-diphenylglycouril) (Pierce, Rockford, Ill.) was dissolved in methylene chloride (1.0 mg/ml), and is pipetted into (1 ml) a sterile/pyrogen free 10 mL vial (86). The vial was rotated and dried under nitrogen to evaporate methylene chloride.

Anion Exchange Resin Filters:

AG1×8 100-200 mesh (Bio-Rad Labs, Richmond, Calif.) was washed using sterile, pyrogen free water. The anion exchange resin is aseptically loaded onto a 0.22 μm filter disc (1.1-1.5 g wet resin/filter unit, Millipore Corp, Milford, Mass.). The resin was washed using following solutions in a sequence (10 mL sterile, pyrogen-free water; 10 ml sterile 0.1 N NaOH; 10 ml pyrogen free water; 10 ml 0.1 N sodium phosphate buffer pH=7.4; and finally by 3.3 ml 0.1 N sodium phosphate buffer with 1% HSA.

Labeling Process:

0.5-0.75 mL of HuCC49ΔCH$_2$ antibody (1.5 mg/ml) was added to a 10 mL vial coated with 1 mg of iodogen. Then, 0.8 ml of phosphate buffered Na$^{124}$I was added to the vial. The reagents are allowed to react for 15 minutes. The free radioactive $^{124}$I was removed using an exchange resin filter disc. 1 mL of 5% sucrose with 0.05% Tween 20 in saline was used elute the labeled antibody.

$^{124}$I-HuCC49ΔCH2-microPET/CT for Tumor Imaging in Xenograft Model

We used microPET and $^{124}$I-HuCC49ΔCH2 to generate high-resolution image for xenograft tumors. The cancer cells (LS174T, 10$^7$ cells) in matrigel/medium (100 μl) were injected subcutaneously into Nu/Nu nude mice. Tumor was allowed to grow for two weeks. Tumor volumes were measured twice per week with calculated tumor volume [(W$^2$× L)/2]. When tumors reach 300 mm$^3$, the animals was injected different dose of $^{124}$I-HuCC49ΔCH2. 18-FDG was used as control. At various time points (1, 24 hrs), we used a Siemens microPET scanner for tumor imaging. The mice were anesthetized with Ketamine (100 mg/kg)/Xylazine (10 mg/kg) and then scanned on a microPET to obtain the PET tumor images. The currently used PET tracer, $^{18}$FDG was used as a control for microPET imaging.

Results:

HuCC49ΔCH2 was labeled with $^{124}$I with iodogen. 67 uCi $^{124}$I-HuCC49ΔCH2 was injected into xenograft mice (LS174T colon cancer). MicroPET was used to image the mice from 1 hr to 24 hrs. Clearly, $^{124}$I-HuCC49ΔCH2 detected xenograft tumor with strong signal. HuCC49ΔCH2 also is targeting to spleen. The signal in thyroid is due to the uptake of free $^{124}$I, while the signal in bladder suggests that the antibody is metabolized in the body, and $^{124}$I is excreted into urine. The thyroid was not blocked in this experiment.

In contrast, when 200 uCi 18FDG was injected into xenograft mouse (LS 174T colon cancer cells). MicroPET showed that FDG is accumulated in heart, eye, muscle, and eliminated from kidney (and bladder). However, the xenograft tumor only show very weak signal. This data is very similar to the clinical data.

These data suggest that $^{124}$I-HuCC49ΔCH2 is a better cancer specific tracer than FDG for PET tumor imaging. Coupled with the demonstrated ability of PET to selectively image $^{124}$I labeled monoclonal antibodies and the ability of anti-tag antibodies to bind to antigen in lymph nodes, the ability to PET image patients with $^{124}$I labeled anti-TAG antibodies for prognostication is demonstrated.

I claim:

1. A method for determining the course of treatment for a patient having adenocarcinoma by detecting an antigen associated with adenocarcinoma, which comprises the steps of:
    (a) forming a conjugate of $^{124}$I and a monoclonal antibody binds tumor-associated antigen (TAG-72);
    (b) introducing said conjugate into a patient suspected of having adenocarcinoma;
    (c) positron emission tomography (PET) scanning said patient to reveal sites of accumulated conjugate, said sites including lymph nodes;
    (d) determining the course of treatment of said patient by the amount of revealed lymph nodes.

2. The method of claim 1, wherein said monoclonal antibody is one or more of B72.3 and CC49 monoclonal antibody and humanized derivatives thereof.

3. The method of claim 2, wherein said monoclonal antibody is one or more of V59, CC49ΔCH$_2$, or HuCC49ΔCH$_2$.

4. The method of claim 1, wherein said determined course of treatment includes surgery that includes use of a hand held probe to locate sites of accumulated conjugate.

* * * * *